United States Patent [19]
Foody et al.

[11] Patent Number: 5,866,407
[45] Date of Patent: Feb. 2, 1999

[54] METHOD AND ENZYME MIXTURE FOR IMPROVED DEPILLING OF COTTON GOODS

[75] Inventors: Brian Foody; Jeffrey S. Tolan, both of Ottawa, Canada

[73] Assignee: Iogen Corporation, Ottawa, Canada

[21] Appl. No.: 819,091

[22] Filed: Mar. 18, 1997

[51] Int. Cl.$^6$ .................................................. C12S 11/00
[52] U.S. Cl. .................... 435/263; 435/209; 510/392; 510/530; 8/401; 8/116.1
[58] Field of Search .................................. 435/209, 263, 435/264, 277; 8/401, 116.1; 510/320, 392, 393, 530

[56] References Cited

U.S. PATENT DOCUMENTS

| | | | |
|---|---|---|---|
| 5,120,463 | 6/1992 | Bjork et al. | 252/174.12 |
| 5,232,851 | 8/1993 | Cox et al. | 435/263 |
| 5,246,853 | 9/1993 | Clarkson et al. | 435/263 |
| 5,290,474 | 3/1994 | Clarkson et al. | 252/174.12 |
| 5,475,101 | 12/1995 | Ward et al. | 536/23.74 |
| 5,525,507 | 6/1996 | Clarkson et al. | 435/263 |
| 5,650,322 | 7/1997 | Clarkson et al. | 435/263 |
| 5,654,193 | 8/1997 | Clarkson et al. | 435/263 |
| 5,705,858 | 1/1998 | Screws et al. | 435/263 |

FOREIGN PATENT DOCUMENTS

| | | |
|---|---|---|
| 89/09259 | 10/1989 | WIPO . |
| 91-17243 | 11/1991 | WIPO . |
| 93/13261 | 7/1993 | WIPO . |
| WO 93/22428 | 11/1993 | WIPO . |
| WO 94/28117 | 12/1994 | WIPO . |
| WO 95/16782 | 6/1995 | WIPO . |
| WO 96/34945 | 11/1996 | WIPO . |

OTHER PUBLICATIONS

Nielsen, et al., *Enzyme Applications (Industrial),* Encyclopedia of Chemical Technology, (Kirk–Othmer Publishers, 1993), vol. 9, pp. 603–604.

Claeyssens and Henrissat, *Specificity Mapping of Cellulolytic Enzymes: Classification into Families of Structurally Related Proteins Confirmed by Biochemical Analysis,* Protein Science vol. 1, pp. 1293–1297 (1992).

Stalbrand, et al., *Cloning and Expression in Saccharomyces cerevisiae of a Trichoderma reesei B–Mannanase Gene Containing a Cellylose Binding Domain,* Applied and Environmental Microbiology, vol. 61, No. 3, pp. 1090–1097 (1995).

Woodward, et al., *Papain Digestion of Crude Trihoderma reesei Cellulase: Purification and Properties of Cellobiohydrolase I and II Core Proteins,* Biotechnol. Appl. Biochem, vol. 19, pp. 141–153 (1994).

Kumar, et al., *Optimizing the Use of Cellulase Enzymes in Finishing Cellulosic Fabrics,* (1995 AATCC conference, Atlanta), pp. 238–247.

Cavaco–Paulo and Rios, *Analysis of the Mechanical Properties of Cellulase Treated Fabrics,* (1996 AATCC conference, Nashville), pp.129–136.

Shoemaker, et al., *Molecular Cloning of Exo–Cellobiohydrolase I Derived from Trichoderma reesei Strain L 27,* Bio/Technology, vol. 1, pp. 691–696 (1983).

Chen, et al., *Nucleotide Sequence and Deduced Primary Structure of Cellobiohydrolase II from Trichoderma reesi,* Bio/Technology, vol. 5, pp. 274–278 (1987).

Penttilä, et al., *Homology Between Cellulase Genes of Trichoderma reesi: Complete Nucleotide Sequence of the Endoglucanase I Gene.,* Gene vol. 45, pp. 253–263 (1986).

Saloheimo, et al., *EGIII, A New Endoglucanase from Trichoderma reesi: The Characterization of Both Gene and Enzyme.,* Gene, vol. 63, pp. 11–20 (1988).

Saloheimo, et al., *A Novel, Small Endoglucanase Gene, EG15, From Trichoderma reesei Isolated by Expression in Yeast,* Molecular Microbiology, vol. 13, No. 2, pp. 219–228 (1994).

King, *Separation Processes,* $2^{nd}$ ed. (McGraw–Hill, 1980), p. 60.

Matsudaira, *Sequence from Picomole Quantities of Proteins Electroblotted Onto Polyvinylidene Difluoride Membranes,* Journal of Biological Chemistry, vol. 262, No. 21, pp. 10035–10038 (1987).

Stone and Williams, *High–Performance Liquid–Chromatographic Peptide Mapping and Amino Acid Analysis in the Sub–Nanomole Range,* Journal of Chromatography, vol. 359, pp. 203–212 (1986).

*Primary Examiner*—William H. Beisner
*Attorney, Agent, or Firm*—Fitzpatrick, Cella, Harper & Scinto

[57] ABSTRACT

A method, and a specific enzyme mixture, for depilling cotton-containing goods, either as unfinished fabric or as finished garments, to create a smooth surface while minimizing the loss of fabric strength. The method consists essentially of removing less than approximately 3.0% of the initial fabric weight with a Trichoderma cellulase enzyme mixture comprising less than naturally-occuring amounts of CBHI, CBHII, EGI and EGIII protein components, and further consisting essentially of at least 80% endoglucanase II (EGII) as the protein component.

12 Claims, 1 Drawing Sheet

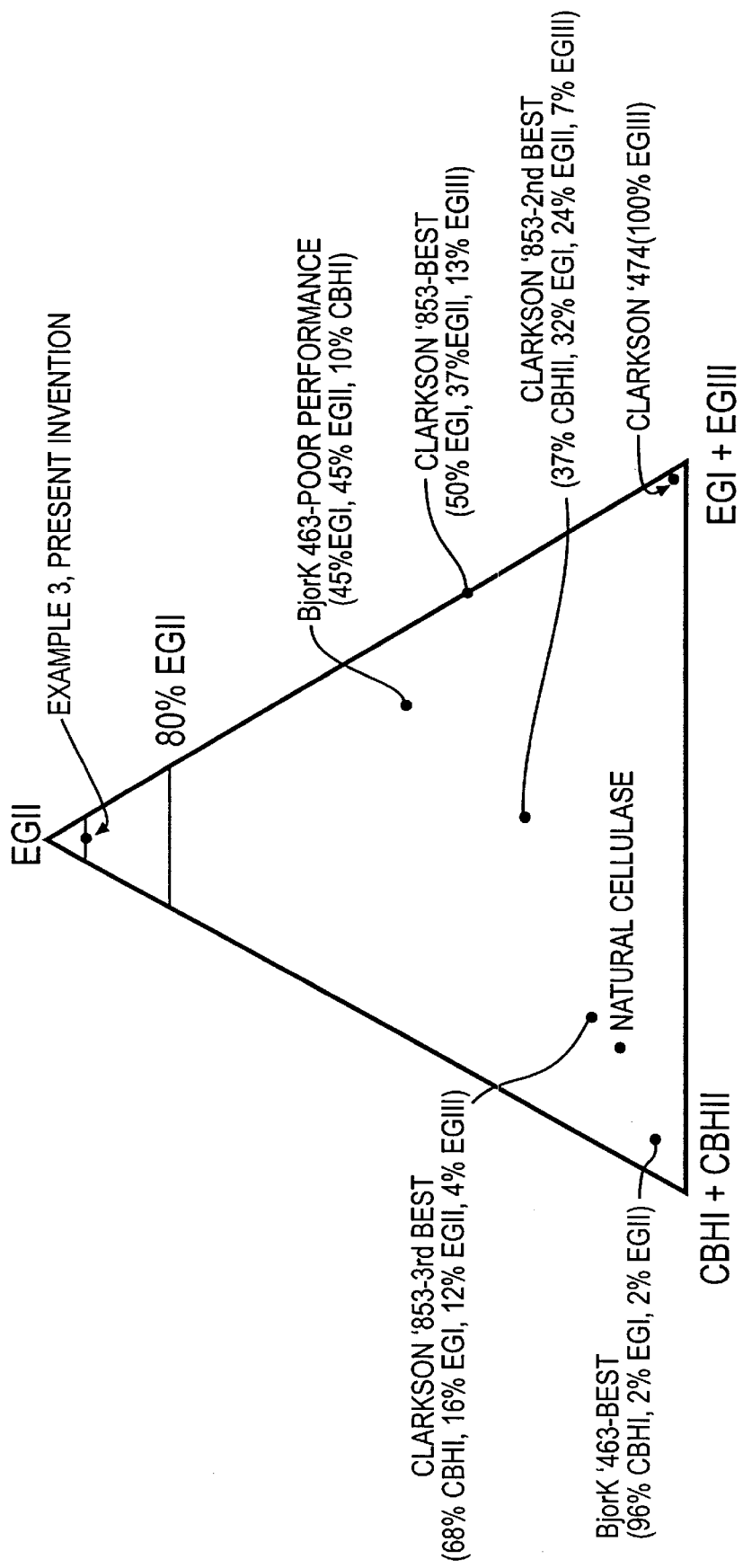

METHOD AND ENZYME MIXTURE FOR IMPROVED DEPILLING OF COTTON GOODS

BACKGROUND OF THE INVENTION

1. Field of the Invention

This invention relates to a depilling treatment of unfinished cotton fabric pieces, or finished garments, with cellulase enzymes, wherein the treatment removes less than approximately 3.0% of the initial fabric weight. More specifically, this invention relates to a method for reducing or preventing fabric strength loss during depilling by employing certain specific cellulase mixtures, and preferably Trichoderma cellulase enzyme mixtures consisting essentially of at least 80% EGII. It has been discovered that with enzyme mixtures enriched in EGII, the removal of pills is more efficient, and fabric destruction during enzyme treatment can reduced by about 88%, relative to the standard commercial cellulase enzymes now in use.

2. Brief Description of the Prior Art

Cellulase enzymes widely are used to improve the appearance and softness of cotton-containing fabrics and garments. As used herein, the terms "cotton goods" denotes finished or unfinished fabrics consisting of cotton or blends of cotton with other fibers.

One widespread application of cellulase enzymes is for treating cotton-containing fabrics so as to "stonewash" denim, in which cellulase enzymes largely have replaced stones for generating the soft, faded denim that is desired by consumers. Further details of cellulase for denim stonewashing can be found in Nielsen, et al, ENZYME APPLICATIONS (INDUSTRIAL), Encyclopedia of Chemical Technology, (Kirk-Othmer Publishers, 1993), vol. 9, p. 603–604 ( referred to hereafter as "Nielsen, et al").

A second widespread application of cellulase enzymes is for treating cotton-containing fabrics so as to remove cotton fuzz and loose surface fibers on or in the fabric, which categorically involves removal of less than approximately 3.0% of the initial fabric weight, and typically less than 1.0%. This process is known variously by the terms "depilling", "biopolishing", "biofinishing", and "reformation". The term "depilling" will be used herein to refer to all such fabric treatments. In depilling, the cellulase treatment smooths the surface of the fabric, which in turn imparts improved softness and appearance, thereby increasing the quality and value of the fabric. Cellulase treatment for depilling also helps to prevent the subsequent formation of fiber pills that make the garments appear worn, and improves the uniformity of the fabric by removing dead or immature cotton. Further details of cellulase for depilling further can be found in Nielsen, et al, at pages 595–604. Depilling of cotton-containing goods is the field of the present invention.

Shear stress is applied to cotton garments during garment manufacturing and in repeated wearing, washing, and tumble drying, and thereby damages the surface. A close look reveals the presence of fibrils ranging in size from a few microns to a few millimeters. The damaged surface scatters light, giving a dull, grayish appearance with decreased color brightness and contrast between different colors. Dust particles also tend to adhere to the damaged areas, adding to the gray appearance. The damaged fibers also make the surface more rigid, thereby decreasing hand, or softness.

Cellulase enzymes hydrolyze exposed beta-1,4 bonds in cellulose. This leads to removal of the fibrils, which are the most exposed part of the fabric. The removal of fibrils is believed to directly improve the softness of the garments and also to lead to better color and cleanliness, both by removing soil attached to the fibrils and by improving the penetration of other cleaning compounds being used. The removal of fibrils initially also helps to prevent a subsequent formation of fibrils.

Cellulase enzymes have several advantages over conventional fabric softeners used to improve the smoothness and sheen on cotton fabrics. Conventional softeners, which are primarily clay or cationic surfactants, coat the fabric and impart a greasy feel, which is undesirable. Softeners also decrease the water absorbency, which is a disadvantage for towels and the like. The enzymes are also preferred from an environmental point of view.

In a typical depilling treatment step during garment manufacturing, fabric (usually dyed), water, buffer, detergents, and enzyme are added to a rotating horizontal or vertical drum jet dyer, washing machine, or other device that provides agitation and shear to the fabric. The treatment is typically for 15 to 120 minutes at 35° C. to 60° C., at a pH of 4 to 6.5 . The ratio of liquor to fabric is usually between 2.5:1 and 6:1, by weight . The amount of cellulase enzyme added typically corresponds to a cellulase activity of about 1,000 to 200,000 CMC units per kilogram of fabric, based on the cellulase assay method of Ghose (1987). After treatment, the enzyme is often destroyed by heating the solution to 70° C. for 10 minutes. The fabric is removed from the machine, dried, and prepared in rolls, sometimes after additional dying. A summary of publications that further describe details of conventional cellulase treatments for depilling of cotton fabrics during manufacturing is found in U.S. Pat. No. 5,232,851, at Column 1.

For a depilling treatment during a laundering step, the cellulase is included in a detergent mixture with the many other ingredients. The other ingredients might include other enzymes, such as proteases, lipases, and cellulases, as well as surfactants, buffers, builders, bleach, anti-redeposition agents, optical brighteners, anti-oxidants, and solubilizers.

One conventional detergent mixture containing cellulase enzymes is further described by Clarkson, et al, in U.S. Pat. No. 5,290,474, (hereafter referred to as "Clarkson '474"). The treatment is typically for 15 to 60 minutes at 20° C. to 70° C., and at a pH of 7 to 9.5. The ratio of liquor to fabric, by weight, is usually between 2.5:1 and 10:1. The amount of cellulase enzyme added typically corresponds to a cellulase activity of about 200 to 40,000 CMC units per kilogram of fabric, based on the cellulase assay method of Ghose (1987).

Cellulase enzymes are used for the depilling of cotton fabrics and of blends of cotton and man-made fibers, including lyocell, rayon, polyester, acrylic, nylon, and cellulose acetate. Further details are illustrated in Clarkson '474, at column 7. Cellulase treatment is carried out on fabrics or sewn garments comprising material made of cotton or cotton blends, with or without a resinous finish. Cellulase depilling may be carried out on fabrics of at least 40% cotton, by weight. However, results are more pronounced and economical if the cotton content is more than 60% by weight, and the best results are obtained if the cotton content is more than 75% by weight.

The cellulase enzymes from one particular genus of wood-rotting fungus, Trichoderma, often are used in depilling applications. Trichoderma cellulases are preferred in textile processing and laundering because of a highly potent action against cotton and other forms of cellulose. Trichoderma cellulase products are commercially available from Iogen Corporation of Ottawa, Ontario, Canada; Genencor International; Novo Nordisk; Enzyme Development Company, and others. Commercial cellulases such as Iogen Cellulase are referred to as "natural" or "complete" cellulases because they contain most, if not all, of the six most prevalent naturally occuring cellulase components: cellobiohydrolase I (CBHI); cellobiohydrolase II (CBHII); endoglucanase I (EGI); endoglucanase II (EGII); endoglucanase III (EGIII) and endoglucanase V (EGV).

The widespread use of complete cellulases for depilling attests to the usefulness of these enzymes. However, one disadvantage of such complete cellulases in depilling treatments is that they can cause a significant loss of strength of the fabric. See Clarkson, et al, U.S. Pat. No. 5,246,853, (hereafter "Clarkson '853"). Loss of strength arises from the action of the cellulase against cellulose on the main body of the fabric, rather than just the desired action against fuzz or pills. Excessive strength loss can cause damage to the fabric, such as pin holes or overly worn spots, and decrease the useful life of the fabric. Decreasing the strength loss would overcome these problems. In addition, decreasing the strength loss would allow one to achieve the desired appearance and softness in fabrics with higher strength than presently achievable. This would result in valuable new products for the industry and the consumer.

To decrease the loss of strength caused by Trichoderma cellulase, efforts have focused on the properties of the individual enzymes that comprise Trichoderma cellulase.

Trichoderma naturally makes a mixture of about two dozen different types of cellulase enzymes, which are individually known as components. Several of the most prevalent of these components have been identified and named, including cellobiohydrolase I (CBHI), cellobiohydrolase II (CBHII), endoglucanase I (EGI), endoglucanase II (EGII), endoglucanase III (EGIII), and endoglucanase V (EGV).

Each of the Trichoderma cellulase enzymes have been classified into an appropriate family of the more than 40 recognized families of hydrolase enzymes. Classification is based on the sequence of amino acids that comprise the enzymes and the three dimensional structure, as described by Claesssens and Henrissat, "SPECIFICITY MAPPING OF CELLULOLYTIC ENZYMES: CLASSIFICATION INTO FAMILIES OF STRUCTURALLY RELATED PROTEINS CONFIRMED BY BIOCHEMICAL ANALYSIS", in Protein Science vol. 1, p. 1293–1297 (1992). The approximate properties, classification, references for amino acid sequences, and proportion of total cellulase protein in the natural enzyme of various Trichoderma cellulase components are summarized, in TABLE 1.

TABLE 1

Trichoderma Cellulase Components

| Enzyme | Mol. wt. | Isoelectric pt. | Family | Reference | Conc. (%) |
|---|---|---|---|---|---|
| CBHI | 63,000 | 4.3 | 7 | A | 50–60 |
| CBHII | 58,000 | 6.0 | 6 | B | 15–18 |
| EGI | 53,000 | 4.6 | 7 | C | 12–15 |
| EGII | 50,000 | 5.3 | 5 | D | 9–11 |
| EGIII | 25,000 | 7.4 | 12 | E | 0–3 |
| EGV | 23,000 | 3.7 | 45 | F | 0–3 |

References:
A. Shoemaker, et al, Molecular Cloning Of Exo-Cellobiohydrolase I Derived From *Trichoderma Reesei* Strain L27. BIO/TECHNOLOGY vol. 1, p. 691–696 (1983).
B. Chen, et al, Nucleotide Sequence And Deduced Primary Structure Of Cellobiohydrolase II From *Trichoderma Reesei*. BIO/TECHNOLOGY, vol. 5, p. 274–278 (1987).
C. Penttila, et al, Homology Between Cellulase Genes Of *Trichoderma Reesei*: Complete Nucleotide Sequence Of The Endoglucanase I Gene. GENE vol. 45, p. 253–263 (1986).
D. Saloheimo, et al, EGIII, A New Endoglucanase From *Trichoderma Reesei*: The Characterization Of Both Gene And Enzyme. GENE, Vol. 63, p. 11–21 (1988).
E. Ward, et al, U.S. Pat. No. 5,475,101
F. Saloheimo, et al, A Novel, Small Endoglucanase Gene, Egl5, From *Trichoderma Reesei* Isolated By Expression In Yeast. MOLECULAR MICROBIOLOGY Vol. 61, p. 1090–1097.

It should be emphasized that the nomenclature used in TABLE 1 is that nomenclature as currently used in this field, and reflects certain changes from earlier nomenclature. For example, the component "EGII" incorrectly and widely had been referred to as—EGII—in early reference works. See, for example, the discussion in Stalbrand, et al, APPLIED AND ENVIRONMENTAL MICROBIOLOGY, vol. 61, p.1090–1097 (1995) ).

One approach followed by prior art workers seeking to decrease the fabric strength loss due to depilling treatments has been to produce what is known as a "truncated version" of cellulase components.

Most cellulase components comprise a catalytic core domain and a cellulose binding domain, separated by a flexible linker that consists of several amino acids. Techniques have been reported for cleaving either the core domain or the binding domain. Techniques also have been reported for using Trichoderma strains with modified DNA, so as to encode only a desired portion of the cellulase. See the published patent document Fowler, et al, WO 95/16782, (hereafter "Fowler '782") The use of protease enzymes to cleave a desired portion of an enzyme also has been reported. See Woodward, et al, BIOTECHNOL. APPL. BIOCHEM., Vol. 19, p. 141–153 (1994).

These truncated cellulases have not solved the problems of strength loss in depilling, as reported by Kumar, et al in "OPTIMIZING THE USE OF CELLULASE ENZYMES IN FINISHING CELLULOSIC FABRICS", 1995 AATCC conference, Atlanta, page 238, (hereafter referred to as "Kumar, et al"). This paper compares performances in depilling (or "biofinishing" as the term appears therein) among Standard Whole Cellulase (which contains the six major cellulase components) and two novel cellulases. One novel cellulase is said to be a "modified acid cellulase", (i.e., a truncated cellulase prepared using procedures of Fowler '782), and does not show any decrease in fabric strength loss during depilling, relative to Standard Whole Cellulase.

A second approach towards decreasing fabric strength loss during depilling treatents has been to choose mixtures of cellulase components that offer advantages relative to the natural mixture. By using well known techniques of genetic engineering or protein processing (described in Clarkson '853), one can alter the relative amounts of cellulase components present.

Bjork et al, U.S. Pat. No. 5,120,463 (hereafter "Bjork '463") and the published patent document Clarkson, et al, WO 93/22428 (hereafter "Clarkson '428") teach that a cellulase enzyme enriched in CBHI components will have less strength loss, as well as superior performance in softening and improving the feel of cotton fabrics, than cellulase with its endoglucanases present. The enzyme mixture with best performance taught by Bjork '463 is 96% CBHI, 2% EGI, and 2% EGII (see TABLE 3 of EXAMPLE 3), with 500 ppm CBHI and 10 ppm of EGI and EGII, divided equally. This mixture also is indicated on FIG. 1 herein as "Bjork '463-best". Very poor performance is indicated for a mixture that is 45% EGI, 45% EGII, and 10% CBHI. This mixture, which is indicated as 10 ppm CBHI and 100 ppm divided between EGI and EGII, also is indicated on FIG. 1 herein as "Bjork '463-poor".

The teachings of Bjork '463 also are supported by the teachings of Cavaco-Paulo and Rios, "ANALYSIS OF THE MECHANICAL PROPERTIES OF CELLULASE TREATED FABRICS", (1996 AATCC conference, Nashville), at p. 129.

Clarkson, et al, U.S. Pat. No. 5,525,507 and Clarkson '853 both allege a particular cellulase enzyme composition for treating cotton fabric to achieve enhanced feel, softness, color enhancement and a stone washed appearance. That particular enzyme composition is taught necessarily to be substantially free of CBHI-type components (column 2, line 57). In one preferred embodiment, the enzyme also is taught necessarily to be free of CBHII components. In a second preferred embodiment, the enzyme is taught necessarily to have at least 10% endoglucanase components. In a third preferred embodiment, the enzyme is taught necessarily to have at least 20% endoglucanase components.

Clarkson '853 alleged best results with a mixture that was 50% EGI, 37% EGII, and 13% EGIII. That mixture is indicated on FIG. 1 herein as "Clarkson '853 best" and is described by Clarkson '853 as "CBHI and CBHII deleted" within Example 16. The necessary proportions of endoglucanases in that mixture as stated above were determined, as follows: In Clarkson '853, at Example 13, the proportions of cellulase components in the natural mixture are listed as being CBHI 45–55%; CBHII 13–15%; EGI 11–13%; EGII 8–11%; EGIII 1–4%. At Example 16, the preferred enzyme is said to have all CBHI and CBHII deleted. If CBHI and CBHII are removed from the total mixture, and the average concentrations of the remaining enzymes are normalized to total 100%, the result will be as stated above.

The second best performance shown by Clarkson '853 was a mixture that was 37% CBHII, 32% EGI, 24% EGII, and 7% EGIII. This mixture is indicated on FIG. 1 as "Clarkson '853 2nd best" and is described by Clarkson '853 as "CBHI deleted". The proportions of enzymes in this mixture as stated above were determined, as follows: In Clarkson '853, at Example 13, the proportions of cellulase components in the natural mixture are listed as being CBHI 45–55%; CBHII 13–15%; EGI 11–13%; EGII 8–11%; EGIII 1–4%. At Example 16, the second-best enzyme is said to have all CBHI deleted. If CBHI is removed from the total mixture, and the average concentrations of the remaining enzymes are normalized to total 100%, the result will be as stated above.

The third best performance shown by Clarkson '853 was a mixture that was 68% CBHI, 16% EGI, 12% EGII, and 4% EGIII. This mixture is indicated on FIG. 1 as "Clarkson '853 3rd best" and is described by Clarkson '853 as "CBHII deleted". The proportions of enzymes in this mixture as stated above were determined, as follows: In Clarkson '853, at Example 13, the proportions of cellulase components in the natural mixture are listed as being CBHI 45–55%; CBHII 13–15%; EGI 11–13%; EGII 8–11%; EGIII 1–4%. At Example 16, the third-best enzyme is said to have all CBHII deleted. If CBHII is removed from the total mixture, and the average concentrations of the remaining enzymes are normalized to total 100%, the result will be as stated above.

The worst performance reported by Clarkson '853 was with the natural cellulase mixture, which also is indicated on FIG. 1 herein.

Clarkson et al, U.S. Pat. No. 5,290,474 (hereafter "Clarkson '474") claim the use of enzymes containing at least 40% EGIII for treating cotton. In a preferred embodiment, the enzyme consists of no more than 5% CBHI components, and at least 70% EGIII. Clarkson '474 claim that this mixture of enzymes is advantageous in that it can be used in alkaline pH (column 3, line 58). There is no suggestion that these mixtures of enzymes result in less strength loss than the mixtures taught by Clarkson '853.

The single example of cellulase mixtures described by Clarkson '474 is substantially pure EGIII. This is indicated on FIG. 1.

The patent publication, Saloheimo, et al, WO 94/28117 relates to uses for the component EGV endoglucanase. This enzyme is taught to be active at alkaline pH and is recommended for use in the textiles industry (page 16, line 19). However, Saloheimo et al neither disclose nor suggest if this enzyme might be superior in depilling performance to other mixtures or components described in the prior art.

Kumar, et al describe measured performances in depilling with Standard Whole Cellulase which contains all of the major cellulase components, and also for two alleged "novel cellulases". One of the novel cellulases so denoted is said to be an "enriched endo-cellulase" but the components present or removed are not identified. Kumar, et al allege that the "enriched endo-cellulase" enzyme causes less strength loss in depilling than would Standard Whole Cellulase. This "enriched endo-cellulase" was not, however, recommended for applications with high abrasion requirements such as heavy cotton and lyocell, since high doses and additional time are said to be required (page 243, middle paragraph).

SUMMARY OF THE INVENTION

The inventors of the present invention have found, surprisingly, that treating cotton goods with a Trichoderma cellulase enzyme mixture consisting essentially of at least 80% EGII component offers superior depilling with less fabric strength loss than other Trichoderma cellulase mixtures. By using specific enzyme mixtures of the present invention, the removal of pills is more efficient, and the amount of fabric destruction during enzyme treatment is reduced by 88%, relative to standard commercial cellulase enzymes used presently for treating cotton fabrics. The invention thereby consists of a method for treating cotton fabrics using specified cellulase mixtures.

BRIEF DESCRIPTION OF THE DRAWING

The FIGURE is a ternary diagram. The composition of Trichoderma cellulases (neglecting the small amount of EGV) can be represented as a ternary diagram with CBHI and CBHII on one vertex; EGI and EGIII on a second vertex; and EGII on the third vertex. Data points representing prior art cellulase compositions, and data points representing the present invention, are labeled with reference to the specification. For further background on the interpretation of the FIGURE, applicants incorporate by reference to the conventions for reading ternary diagrams as explained by C. Judson King in SEPARATION PROCESSES, (McGraw-Hill, 1980), at page 60. Using those conventions, the concentration of a species is read along the line from the vertex labelled with the species to the opposite side. The concentration of a species is 100% at the vertex labeled with a first species, and decreases linearly along any line drawn from that point, reaching a value of zero for that first species where that line intersects an opposite vertex, or side.

DETAILED DESCRIPTION OF PREFERRED EMBODIMENTS

It has been discoverred that cotton goods treated with a Trichoderma cellulase mixture consisting essentially of at least 80% EGII component exhibit a smooth appearance and soft feel, with less loss of fabric strength than goods treated with other Trichoderma cellulase preparations. The Trichoderma cellulase mixtures of the invention offer superior depilling with a lower fabric strength loss than other Trichoderma cellulase mixtures.

Preferred compositions of cellulase mixtures according to the present invention also are shown in the FIGURE. To better appreciate the scope of the present invention, and for purposes of enabling practice of the present invention, certain terms now will be explained, or more particularly defined.

As used herein the term "cotton goods" refers to fabrics, either as piece goods or sewn into garments, comprising cotton or cotton blends, and either before or after dying and with or without a resinous finish. Hence, the term "cotton goods" is broader than "cotton fabric", as customarily used in in the garment industry to refers to the material or piece goods before sewing. The term "goods" should be viewed as a shorthand abbreviation for "fabric or garments, unfinished or finished" and not to connote any preference as to a preferred practice of the invention.

In a preferred embodiment, the cotton goods consist of cotton or blends of cotton with non-cotton fibers, such as nylon, acrylic, polyester, rayon, or lyocell, such that the cotton content of the fabric is more than 40% by weight. More preferably, the cotton content is more than 60% by weight. Most preferably, the cotton content is more than 75% by weight.

The term "treatment" refers to depilling treatments carried out during the manufacturing process or in subsequent laundering. In either case, treatment is carried out by adding cotton goods to a rotating horizontal or vertical drum jet dyer, washing machine, or other device that contains the fabric, water, buffer, detergents, surfactants, and cellulase enzyme while providing agitation and shear to the fabric. The treatment is often followed by a rinsing with water to remove the spent chemicals and debris from the fabric, including the loose fibrils. After treatment, the fabric is removed from the machine and dried.

The treatment conditions used in the following examples are believed consistent with those generally used for depilling. When depilling takes place in a typical manufacturing process, treatment time is about 15 to about 120 minutes; treatment temperature is about 35° C. to about 60° C., the ratio of liquor to fabric is between about 2.5:1 and about 10:1 by weight, and the pH is about 4.0 to about 6.0. When depilling takes place in a typical laundering, the treatment time is about 10 to 60 minutes, the treatment temperature is about 20° C. to about 70° C., the ratio of liquor to fabric is between about 2.5:1 and about 10:1 by weight, and the pH is about 7.0 to about 9.5.

The amount of cellulase mixture used to depill depends on the concentration of active protein in the cellulase mixture, the amount of cotton goods being treated, and the desired amount of depilling effect, the time of treatment and other parameters well-known to those skilled in the art. When used for depilling in a typical manufacturing process, the preferred amount of Trichoderma cellulase mixture is generally between about 2,000 and about 100,000 CMC units of enzyme per kg of fabric and more preferably between about 10,000 and about 40,000 CMC units per kg of fabric. When used for depilling in a typical laundering, the preferred amount of Trichoderma cellulase mixture is generally between about 200 and about 40,000 CMC units of enzyme per kg of fabric and more preferably between about 1,000 and about 10,000 CMC units per kg of fabric.

One option for controlling the action of the enzyme, which is recommended but not required, is to destroy the enzyme after treatment by heating the solution to about 70° C. for 10 minutes, by adding chemicals that destroy enzyme activity, or by immediately drying the fabric.

The terms "CBHI", "CBHII", "EGI", "EGII", "EGIII", and "EGV" refer to the most prevalent protein components known to be made by Trichoderma naturally, and are classified as described hereinbefore, within TABLE 1.

It is contemplated that the modified Trichoderma cellulase mixtures of the present invention also may be generated as cellulase mixtures which are obtained from a Trichoderma sp. that has been genetically modified so as to overproduce, underproduce or not produce one or more of the CBH or EG components, using techniques generally known, as suggested by Bjork '463 and Clarkson '853.

Hence, these endoglucanases and cellobiohydrolases may include not only enzymes that are a part of the natural Trichoderma cellulase enzyme mixture, but also such modified cellulase mixtures as truncated cellulase proteins comprising either the binding domain or the core domain of the CBHs or EGs, or a portion or derivative thereof. See, generally, Fowler '782.

Other contemplated techniques for creating modified cellulase mixtures may include alterations in the degree of glycosylation, or substitution(s) of amino acid(s) in the primary structure of the cellulases or truncated cellulases. It is also contemplated that any natural or modified components of Trichoderma cellulases, such as those outlined above, shall be considered as Trichoderma cellulase components, even if they are produced in a genetically modified host microorganism, other than Trichoderma.

The term "total cellulase protein" refers to the sum total of CBHI, CBHII, EGI, EGII, EGIII, EGV, and other active Trichoderma cellulase protein components. This term is meant to exclude non-cellulase enzymes, such as amylase, protease, hemicellulase, and lipase. This term is also meant to exclude cellulase protein that may still be present, but was inactivated by heat, chemical, or other means.

The term "natural cellulase preparation" refers to Trichoderma cellulase compositions that are typically produced in a submerged culture by the fungus Trichoderma. Methods for their production and recovery are well documented in the literature and widely known to those skilled in the art. Commercial sources for these enzymes include Iogen Corporation, Genencor International, Novo Nordisk, Sigma Chemicals, and Enzyme Development Corporation.

In practicing the invention, at least 80% of the total cellulase protein in the cellulase mixtures will be the EGII component. In a preferred embodiment, at least 90% of the total cellulase protein is the EGII component. In a more preferred embodiment, at least 95% of the total cellulase protein is the EGII component.

Several methods described in the literature are useful for producing the cellulase enzyme mixtures of the present invention. For example, Trichoderma strains in theory may be genetically modified to delete the production of the CBHI, CBHII, EGI, EGIII, and EGV components. See Clarkson '474 and Clarkson '428. Alternatively, the components may be removed or purified from a natural cellulase preparation by using ion exchange chromatography to produce the mixtures desired. This last technique in particular has been illustrated in EXAMPLES 1 and 2.

To determine the relative amounts of each of the cellulase components in a cellulase mixture, the method that would most commonly be used would be to run a standard isoelectric focusing (IEF) gel and comparing the protein profile with that for purified standards of each component. A description of this method is found in EXAMPLE 2. This method is sufficient for the routine analysis of cellulase preparations, but does not unequivocally identify the proteins. The preferred, 95% EGII mixture taught herein reveals a single cellulase protein band, with an isoelectric point that is between approximately 5.0 and 5.6, depending upon the precision of the measuring equipment, with the isoelectric point typically 5.3.

The definitive procedure is to determine the amino acid sequence of each of the proteins to verify that they match those previously published for the whole or truncated Trichoderma cellulase components, as listed in the references to TABLE 1. The determination of amino acid sequences is described by several references familiar to those skilled in the art, including P. Matsudaira, SEQUENCE FROM PICOMOLE QUANTITIES OF PROTEINS ELECTROBLOTTED ONTO POLYVINYLIDENE DIFLUORIDE MEMBRANES, Journal of Biological Chemistry, vol. 262, p.10035–10038 (1987), and K. L. Stone and K. R. Williams, HIGH PERFORMANCE LIQUID CHROMATOGRAPHIC PEPTIDE MAPPING AND AMINO ACID ANALYSIS IN THE SUBNANOMOLE RANGE, Journal of Chromatography, vol. 359, p.203–212 (1986).

The cellulase mixtures of this invention may be combined with various adjuvants as known to those skilled in the art. For example, a surfactant (anionic or nonionic) compatible with these cellulase components may be useful. Other materials possibly useful with these cellulase mixtures include fillers, solvents, buffers, enzyme stabilizers, pH control agents, enzyme activators, builders, other anti-redeposition agents and the like.

The enzyme composition may be formulated as a solid product wherein the solid may be granular, spray dried or agglomerated. Alternatively, the enzyme composition may be formulated as a liquid, gel, or a paste product. A liquid preparation is preferred herein.

EXAMPLES OF THE PRESENT INVENTION

The above detailed description discloses the compositions of the invention and methods of making and using the compositions in the "depilling" of fabric clothing items. Other choices of wash conditions such as concentration, measurement, pH, temperature, and the like, will be evident to those skilled in the art based on the teachings herein. The following specific examples further illustrate benefits and advantages from the present invention.

EXAMPLE 1

Enrichment of EGII from a Trichoderma cellulase composition

Approximately 10 liters of a commercial Trichoderma cellulase preparation known as Iogen Cellulase (commercially available from Iogen Corporation, Ottawa, Ontario, Canada), was adjusted to pH 7 with sodium hydroxide, dialysed across an Amicon 10,000 molecular weight cutoff membrane to a conductivity of 580 microsiemens and diluted to a protein concentration of 8 mg/ml with a pH of 7. The cellulase was fed onto a 3 liter column of Q-Sepharose anion exchange resin (commercially available from Pharmacia Biotech, of Uppsala, Sweden). A total of 9 liters of feed was added to the column. At these conditions, those components with low isoelectric points, (including CBHI, EGI, and EGV) bind to the column more tightly than the other components. CBHI and EGI are, therefore, the most prominent bound components. At this point, the column was washed with 9 liters of 2 mM sodium phosphate buffer solution, pH 7, conductivity 370 microsiemens. The eluent was collected, adjusted to pH 4 with hydrochloric acid, and dialyzed to 200 microsiemens conductivity across an Amicon 10,000 molecular weight cutoff membrane.

The resulting solution had most of the CBHI and EGI removed from the initial cellulase mixture, as verified by the diminished intensity of these bands on IEF gels. The EGV was probably also removed, although the concentration of EGV is so low in the initial cellulase mixture as to make a quantitative assessment of its concentration difficult.

At this point, the dialyzed eluent (10 g/L protein) was fed to a 60 ml column of S-Sepharose cation exchange resin, (commercially available from Pharmacia Biotech). A total of 60 ml of feed was added to the column, followed by washing with 180 ml of 2 mM sodium acetate buffer, pH 4. This resin binds most tightly to the components with lower isoelectric points, which would include EGII. The wash eluent contained primarily CBHII as well as EGIII and was discarded.

A solution of 10 mM sodium acetate buffer, pH 4, was then fed to the column to desorb the EGII. The first 300 ml of eluent corresponding to this feed was collected in 10 ml fractions and then analyzed to determine the exact components present, by the steps of EXAMPLE 2.

EXAMPLE 2

Analysis And Identification Of Cellulase Components By IEF

A standard polyacrylamide gel isoelectric focusing (IEF) technique was used to analyze the composition of cellulase components. This method is described in ISOELECTRIC FOCUSING PRINCIPLES AND METHODS, (Pharmacia Fine Chemicals, 1982). The gels were 5% polyacrylamide and were run at pH 3 to 10. The proteins were stained with Coomassie blue and destained with a mixture of methanol and acetic acid.

The samples analyzed included aliquots of the 10 ml fractions collected in the elution of EXAMPLE 1. These aliquots were diluted to 2 to 5 mg/ml of protein. A 50 microliter sample of Iogen Cellulase was also analyzed, as were enriched samples of CBHI, CBHII, EGI, and EGII, and isoelectric point markers at several isoelectric points.

Iogen Cellulase has protein bands present corresponding to all of the single components, plus several other proteins. The fractions from the eluent from EXAMPLE 1 were deficient in CBHI, CBHII, EGI, EGIII, and EGV, as indicated by the absence of bands corresponding to these proteins at isoelectric points of 4.3, 6.0, 4.6, 7.7, and 3.7, respectively. In the fractions from the eluent from EXAMPLE 1, only one protein band was visible, at an isoelectric point of 5.3. This band corresponds to EGII, as indicated by the isoelectric point and subsequent observation of a high activity against carboxymethylcellulose and a low activity against filter paper.

EGII is the only major band visible in these fractions. It accounts for 95% of the total cellulase protein present with the balance consisting of CBHI, CBHII, EGI, and EGIII. Quantification of protein concentration is carried out by scanning laser densitometry, such as by using a Sharp JX 330 scanner with ImageMaster software, (commercially available from Pharmacia Biotech).

The 10 ml fractions consisting primarily of EGII were combined and concentrated by ultrafiltration to 6.5 g/L, then stored frozen. This enzyme was denoted as "enriched EGII" and used for further experiments.

EXAMPLE 3

Improved Fines Removal By Enriched EGII

Four Trichoderma cellulase enzyme preparations were evalauted for performance in depilling applications, as follows:

1. The enriched EGII cellulase of EXAMPLE 2.

2. A cellulase preparation of 50% EGI, 37% EGII, and 13% EGIII. This preparation is free of CBHI. This preparation matches the best mixture of Clarkson '853, as indicated in the FIGURE. The proportions of endoglucanases in this mixture were determined, as follows:

In Clarkson '853, at Example 13, the proportions of cellulase components in the natural mixture are listed as being CBHI 45–55%; CBHII 13–15%; EGI 11–13%; EGII 8–11%; EGIII 1–4%. At Example 16, the best and preferred enzyme is said to have all CBHI and CBHII deleted. If CBHI and CBHII are removed from the total mixture, and the average concentrations of the remaining enzymes are normalized to total 100%, the result will be as stated above.

3. A cellulase preparation with 96% CBHI, 2% EGI, and 2% EGII. This preparation matches the best of the mixtures reported by Bjork '463. The proportions of enzymes in the mixture were determined, as follows:

In Bjork '463, at Example 3, Table III, it is taught that the best mixture of enzymes is 500 ppm CBHI and 20 ppm of EGI plus EGII, and those being in equal amounts (see line 45). Such a mixture of 500 ppm CBHI, 10 ppm EGI, and 10 ppm EGII will have proportions, as stated above.

4. Iogen Cellulase, a commercial cellulase product that has the natural set of cellulase enzymes in the proportions described in TABLE 1 and shown in the FIGURE.

The evaluation phase for these four compositions consisted of two measurements: (1) Removal of fines from fabric, which is desirable, and (2) Destruction of fabric, which is undesirable. EXAMPLE 3 discusses fines removal and EXAMPLE 4 discusses destruction of fabric.

The depilling evaluation was carried out as follows. The fabric consisted of an undyed blend of 60% Tencel® and 40% cotton. Tencel is a trademark of Courtaulds Ltd for its brand of lyocell fabric. The fabric surface was highly pilled in a manner typical of such fabric in the intermediate stages of manufacturing. A circular piece of fabric of diameter 7.8 cm, weight 1 gram, was placed on the bottom of a 250 ml Erlenmeyer flat-bottomed flask. A total of 145 steel balls of diameter 4.76 millimeters (total weight 63 g) were placed on the fabric. The enzymes were diluted in 50 mM citrate buffer (pH 4.8) such that 7.5 mg of protein was added to 6 grams of buffer. The enzyme/buffer solution was preheated to 50° C. in a water bath, then added to the fabric. The flasks were shaken at 225 RPM for 1 hour in a New Brunswick gyrotory shaker. At this point, the contents of the flask were filtered over pre-weighed glass microfiber filter paper. The steel balls were removed, and the flask and filter paper were washed three times with deionized water. The filter paper was then dried for 90 minutes at 100° C. in an oven. The amount of fines collected was determined by subtracting the initial weight of filter paper from the final weight and then expressing the result as a percentage of the initial weight of fabric.

The results are shown in TABLE 2. The EGII enriched cellulase released more fines from the fabric than did the cellulases of either Clarkson '853, Clarkson '428 or the Iogen commercial enzyme. The advantage in fines removal by enriched EGII over the other enzymes also was evident from a visual inspection of the fabric. By removing more fines from the fabric, the enriched EHII produces a smoother, more acceptable appearance that the other enzymes tested. Alternatively, a given level of fines removal can be achieved with less enriched EGII than the other enzymes, which can result in a more economical depilling treatment.

TABLE 2

Depilling Results By Enriched EGII And Other Enzymes.

| Enzyme (@7.5 mg/gram fabric) | Fines removed (% of initial fabric weight) |
|---|---|
| Enriched EGII (95% EGII) | 0.80 |
| Clarkson '853 (50% EGI, 37% EGII, 13% EGIII) | 0.45 |
| Clarkson '428 (90% CBHI, 5% EGI, 5% EGII) | 0.05 |
| Iogen Cellulase (45–55% CBHI; 13–15% CBHII; 11–13% EGI; 8–11% EGII; 1–4%. EGIII) | 0.65 |

EXAMPLE 4

Decreased Fiber Destruction By Enriched EGII Cellulase

The second part of the enzyme evaluation is the measurement of fabric destruction during depilling. This evaluation is carried out using that amount of enzyme (mg. per gram of fabric)—for each of the four test enzymes mixtures—that will achieve a "total" fines removal (usually about 0.6% by weight of initial fabric weight) and then measuring the amount of glucose sugar produced to deduce how much fabric fiber also was destroyed. Ideally, a removal of 0.6% of initial fabric weight will correspond to removing only the undesirable fines, with little if any additional fiber destruction inside the fabric structure.

This example used the same enzymes as EXAMPLE 3. The depilling treatments and collections of filtrates were carried out using the same techniques as in EXAMPLE 3, except the dosage of each enzyme was chosen so that upon examination all existing fines (about 0.6% of the initial fabric weight in the test samples) are shown to be removed.

The amount of fabric—beyond the fines—also destroyed to glucose was determined as follows. The filtrates had sulfuric acid added to a concentration of 20 grams per liter and were heated to 121° C. in a steam autoclave for 1 hour. The flasks were then cooled to ambient temperature and adjusted to pH 5 with sodium citrate buffer solution. The glucose concentration of the filtrates was then measured on a Dionex pulsed amperometric HPLC (Dionex Co., San Jose, Calif.). The glucose concentration was related to the initial weight of fabric to determine the percentage conversion to glucose.

The procedures were carried out with several levels of cellulase to establish the level required to remove fines from four fabric samples, each measured to have about 0.6% of initial fabric weight as fines. The level required for Enriched EGII was only 6.0 milligrams of enzyme per gram of fabric. The enzyme of Clarkson '853 required 9.0 mg/gram. The enzyme of Clarkson '428 required 45.0 mg/gram. The Iogen cellulase required 7.2 mg/gram. Once a level of cellase for a complete depilling was identified, the amount of fabric also destroyed to glucose by that level of cellulase was derivable, since in each test the glucose attributable to fines removal alone is a constant. The results are shown in TABLE 3.

The enriched EGII cellulase caused far less undesirable fabric destruction in the complete depilling tests than any of the other three enzyme test mixtures evaluated: the commercial cellulase, the enzyme of Clarkson '853, and the enzyme of Clarkson '428. The decrease in fabric destruction by the enriched EGII cellulase indicates that a stronger fabric results from enriched EGII than from treatment with any other known mixtures.

For a given depilling treatment, the enriched EGII cellulase causes 63% less destruction of fabric than the cellulase mixtures taught by Clarkson '853.

For a given depilling treatment, the enriched EGII cellulase causes 80% less destruction of fabric than the cellulase mixtures taught by Clarkson '428.

For a given depilling treatment, the enriched EGII cellulase causes 88% less destruction of fabric than the standard cellulase mixtures used for commercial depilling treatments.

TABLE 3

Depilling Results By Depleted Cellulase And Other Enzymes.

| Enzyme | Cellulase Level (mg./gram fabric) | Fabric destruction* (% of initial fabric weight) |
| --- | --- | --- |
| Enriched EGII (95% EGII) | 6.0 | 0.30 |
| Clarkson '853 (50% EGI, 37% EGII, 13% EGIII) | 9.0 | 0.80 |
| Clarkson '428 (90% CBHI, 5% EGI, 5% EGII) | 45.0 | 1.50 |
| Iogen Cellulase | 7.2 | 2.50 |

*after removing all fines (about 0.6% of initial fabric weight)

While preferred embodiments of our invention have been shown and described, the invention is to be defined solely by the scope of the appended claims, including any equivalent for each recited claim element that would occur to one of ordinary skill and would not be precluded by prior art considerations.

We claim:

1. In a method of enzymatic depilling of cotton goods, wherein the improvement comprises minimizing the loss of fabric strength while creating a smooth surface appearance by treating the goods with a Trichoderma cellulase enzyme composition consisting essentially of a cellulase protein content that is at least 80% endoglucanase II (EGII).

2. The improved method according to claim 1, the cellulase enzyme consisting essentially of a cellulase protein content that is at least 95% EGII.

3. The improved method according to claim 1, the cellulase enzyme consisting essentially of a single cellulase protein band, having an isoelectric point that is between approximately 5.0 and 5.6.

4. The improved method according to claim 3, the cellulase enzyme consisting essentially of a single cellulase protein band having an isoelectric point that is approximately 5.3, while exhibiting a high activity against carboxymethylcellulose and a low activity against filter paper, and the cotton goods depilling is for removal of less than approximately 3.0% of the initial cotton goods weight.

5. A composition for the enzymatic depilling of cotton goods which minimizes loss of fabric strength while creating a smooth surface appearance on said goods, consisting essentially of a Trichoderma cellulase enzyme mixture with a cellulase protein content that is at least 80% endoglucanase II (EGII).

6. The enzyme composition according to claim 5, consisting essentially of a cellulase protein content that is at least 95% EGII.

7. The enzyme composition according to claim 5, consisting essentially of a single cellulase protein band, having an isoelectric point that is between approximately 5.0 and 5.6.

8. The enzyme composition according to claim 7, consisting essentially of a single cellulase protein band having an isoelectric point that is approximately 5.3, while exhibiting a high activity against carboxymethylcellulose and a low activity against filter paper and the enzymatic depilling is to remove less than approximately 3.0% of the initial cotton goods weight.

9. A method for treating cotton goods to create a smooth surface while minimizing the loss of fabric strength, consisting essentially of treating the goods with a Trichoderma cellulase enzyme composition that has decreased amounts of naturally occuring CBHI, CBHII, EGI and EGIII protein components, so as to result in a cellulase protein content that is at least 80% endoglucanase II (EGII).

10. The method according to claim 9, wherein the cellulase protein content is at least 95% EGII.

11. The method according to claim 9, wherein the cellulase protein content consists essentially of a single cellulase protein band, having an isoelectric point that is between approximately 5.0 and 5.6.

12. The method according to claim 11, wherein the cellulase protein content consists essentially of a single cellulase protein band having an isoelectric point that is approximately 5.3, while exhibiting a high activity against carboxymethylcellulose and a low activity against filter paper, and the cotton goods treatment is for removal of less than approximately 3.0% of the initial cotton goods weight.

* * * * *